United States Patent
Lee et al.

(10) Patent No.: US 7,186,751 B2
(45) Date of Patent: Mar. 6, 2007

(54) INJECTABLE COMPOSITION OF PACLITAXEL

(75) Inventors: Woo-Young Lee, Suwon (KR); Sang-Heon Lee, Kyunggi-do (KR); Kye-Hyun Kim, Seoul (KR)

(73) Assignee: Choongwae Pharma Corporation, Seoul (KR)

( * ) Notice: Subject to any disclaimer, the term of this patent is extended or adjusted under 35 U.S.C. 154(b) by 120 days.

(21) Appl. No.: 10/489,224

(22) PCT Filed: Sep. 9, 2002

(86) PCT No.: PCT/KR02/01696

§ 371 (c)(1),
(2), (4) Date: Sep. 10, 2004

(87) PCT Pub. No.: WO03/022247

PCT Pub. Date: Mar. 20, 2003

(65) Prior Publication Data

US 2005/0026995 A1    Feb. 3, 2005

(30) Foreign Application Priority Data

Sep. 10, 2001    (KR) .............................. 2001-55511

(51) Int. Cl.
*A61K 31/335*    (2006.01)
(52) U.S. Cl. ................................... 514/449
(58) Field of Classification Search ................. 514/449
See application file for complete search history.

(56) References Cited

U.S. PATENT DOCUMENTS

| | | | | |
|---|---|---|---|---|
| 5,403,858 A | * | 4/1995 | Bastard et al. | 514/449 |
| 5,504,102 A | * | 4/1996 | Agharkar et al. | 514/449 |
| 5,733,888 A | * | 3/1998 | Carver et al. | 514/449 |
| 5,922,754 A | * | 7/1999 | Burchett et al. | 514/449 |
| 6,046,230 A | | 4/2000 | Chung et al. | 514/449 |

FOREIGN PATENT DOCUMENTS

| | | |
|---|---|---|
| EP | 583955 A2 | 2/1994 |
| EP | 645145 A2 | 3/1995 |
| WO | WO 94/12198 | 6/1994 |
| WO | WO 99/49848 | 10/1999 |

OTHER PUBLICATIONS

David R. Lide, ed., CRC Handbook of Chemistry and Physics, 86th Edition, Taylor and Francis, Boca Raton, FL, 2006.*
BASF, Cremophor RH Grade Technical Leaflet, May 1992. Accessed from <http://www.basf-korea.co.kr/02_products/04_finechemicals/document/cosmetic/tech/surfactants/down.asp?file=cremophorrhgrades.pdf> on Apr. 20, 2006.*
Alkan-Onyuksel, H. et al., "A Mixed Micellar Formulation Suitable for the Parenteral Administration of Taxol," *Pharmaceutical Research* 11(2): 206-212, Feb. 1994.
Sharma and Straubinger, "Novel taxol formulations: preparation and characterization of taxol-containing liposomes," *Pharm. Res.* 11(6): 889-896, 1994.
Sharma, D. et al., "Novel Taxol® Formulation: Polyvinylpyrrolidone Nanoparticle-Encapsulated Taxol® for Drug Delivery in Cancer Therapy," *Oncology Research* 8(7/8): 281-286, 1996.
Patent Abstracts of Japan, JP 01-116082, May 9, 1989. Available from http://www.jpo.go.jp.
Patent Abstracts of Japan, JP 06-206815, Jul. 26, 1994. Available from http://www.jpo.go.jp.

* cited by examiner

*Primary Examiner*—Phyllis Spivack
*Assistant Examiner*—James D. Anderson
(74) *Attorney, Agent, or Firm*—Seed IP Law Group PLLC

(57) ABSTRACT

The disclosure concerns an injectable composition of paclitaxel, more particularly, an injectable composition of paclitaxel having excellent anticancer effect comprising solubilizer such as polyoxyl hydrogenated castor oil, anhydrous ethanol and stabilizer such as N-acetyl amino acid. The injectable compositions of paclitaxel provide a medical effect higher than that of the known compositions showing not only a lower toxicity but also superior solubility of paclitaxel and stability at room temperature, thus enabling venous injection by having fine particles.

6 Claims, No Drawings

INJECTABLE COMPOSITION OF PACLITAXEL

CROSS-REFERENCE TO RELATED APPLICATION

This application claims the benefit of Korean Application No. 2001/0055511 filed Sep. 10, 2001.

FIELD OF THE INVENTION

The present invention relates to injectable compositions of paclitaxel. More particularly, it relates to injectable compositions of paclitaxel comprising paclitaxel with superior anti-cancer effect, anhydrous ethanol, solubilizers such as polyoxyl hydrogenated castor oil, and stabilizers such as N-acetyl amino acid.

BACKGROUND OF THE INVENTION

Paclitaxel is an alkaloid extracted from the bark of a yew, which promotes the formation of microtubules from tubulin dimmers. It is also used as an antimicrotubule agent stabilizing the microtubules by preventing depolymerization, which shows superior anti-cancer effect against ovarian cancer, breast cancer, head and neck cancer and non-small cell lung cancer.

Since the above paclitaxel has a very low solubility against water, 30 μg/ml, and is physically unstable, research on paclitaxel is being performed. Especially, due to its non-solubility, it is difficult for it to be used as an injection. Further, the paclitaxel injection has various problems such as low stability and toxicity caused by solubilizer, and various researches are being performed to overcome such problems.

Prior art discloses a method [PCT/AU93/00599] for preparing a solution whose pH is lower than 8.1 by adding organic acid to paclitaxel in order to enhance drug stability. However, since the solubilizer used in this method, polyoxyethyleneglycerol triricinolate, Cremophor EL™ (hereinafter referred to as "Cremophor EL"), causes a serious hypersensitive reaction and separates plasticizer from polyvinyl chloride resin set, it is not preferable to be used as an injection.

Hereupon, in order to solve such problems, the use of a liposome formulation prepared by using phosphatidylcholine as a solubilizer has excluded the use of Cremophor EL™, but still, the low solubility (0.8 mg/ml) has not been improved and the stability of the above liposome formulation is being questioned, and thus, there is difficulty in mass production [*Pharm. Res.*, 1994, 11(2), 206–212; *Pharm. Res.*, 1994, 11(6), 889–896].

Recently, researches on improving solubility by chemically combining paclitaxel with a biodegradable block copolymer comprising hydrophilic region and hydrophobic region, as a solubilizer are actively being performed, but this method has difficulty in being used as a drug due to the polymerization of the two hydrophobic and hydrophilic regions, the difficulty such as evaporation and freeze drying process during the manufacturing process, and the accompanying increase of the production cost and the decrease of biocompatibility [JP 116,082/89; JP 206,815/94; EP 0 583 955 A2].

A preparation marketed in the name of Taxol® is disclosed, which is a liquid preparation wherein 30 mg of paclitaxel is dissolved in 5 ml of a mixed solution of absolute alcohol/Cremophor EL™ (1:1). When being administered, the solution is diluted with physiological saline or 5% glucose solution to 0.6–1.2 mg/ml and only 175 mg/m² is instilled and administered into the veins throughout 6–24 hours. However, Cremophor EL™ which is used as the above solubilizer contains toxicity itself which causes serious toxicities such as hypersensitivity, dyspnea and flushing. Thus, in order to minimize the hypersensitive reactions which are side effects caused when taxol is administered, adrenocortical hormone(Dexamethasone), antihistimines(Diphenhydramine) and H2 antagonist(Cimetidine) are administered in advance. Further, due to the problem that titer declines by paclitaxel degradation caused by the decrease of formulation stability, it is required to be stored at a low temperature. Also, various side effects are being reported such as the fact that it must go through a filtering progress when being administered in human body since particles are generated with the progress of time.

Hereupon, in order to overcome the above problems, the present inventors studied injectable compositions of paclitaxel comprising low toxic solubilizer and stabilizer, and thus, found out that polyoxyl hydrogenated castor oil is used as a solubilizer, and N-acetyl amino acid is used as a stabilizer to prepare injectable compositions of paclitaxel containing absolute alcohol. Further, the present inventors completed the invention by finding out that the compositions of the present invention shows more than the same pharmaceutical effects compared with the known injectable compositions of paclitaxel, and that the drug stability increases at room temperature, and that toxicity decreases.

SUMMARY OF THE INVENTION

It is an object of the present invention to provide antitumoric injectable compositions of paclitaxel with reduced toxicity.

More particularly, it is an object of the present invention to provide injectable compositions of paclitaxel, comprising paclitaxel, anhydrous ethanol, polyoxyl hydrogenated castor oil as solubilizer, and N-acetyl amino acid as stabilizer.

DISCLOSURE OF THE INVENTION

To accomplish the said object, the present invention provides injectable compositions of paclitaxel comprising paclitaxel, solubilizer, stabilizer and anhydrous ethanol, wherein the said solubilizer is polyoxyl hydrogenated castor oil.

Also, the present invention provides injectable compositions of paclitaxel comprising paclitaxel, solubilizer, stabilizer and anhydrous ethanol, wherein the said stabilizer is N-acetyl amino acid.

The present invention will be explained in more detail in the following.

The present invention provides injectable compositions of paclitaxel comprising 0.1~5.0 weight percent of paclitaxel, 95~99.89 weight percent of polyoxyl hydrogenated castor oil and anhydrous ethanol, and 0.01~1.0 weight percent of a stabilizer.

The said paclitaxel is 5 β, 20-epoxy-1,2α,4,7β,10β,13α-hexahydroxytaxe-11-en-9-one-4,10-diacetate-2-benzoate-13-ester specifying (2R, 3S)-N-benzoyl-3-phenylisoserine, as a compound of taxane series. The said material is known to have pharmacological effects as antitumor agent. Also, the pharmacological effect of paclitaxel is to stimulate the formation of microtubule from tubulin dimers, and to prevent from depolymerization, thus is used as antimicrotubule agent stabilizing the microtubule.

The injectable compositions of paclitaxel, according to the present invention contain 0.1~5.0 weight percent of paclitaxel.

Solubility of the said paclitaxel in water is 30 μg/ml, thus use of solubilizer makes the solubility of the paclitaxel in water increased. Solutions prepared by mixing the said solubilizer and anhydrous ethanol in a ratio of 30:70~70:30 in volume/volume is used to dissolve non-soluble paclitaxel. The paciltaxel is dissolved in the said solution prepared by mixing the said solubilizer and anhydrous ethanol, therein the stabilizer is added to the said solution. Thus paclitaxel uniformly dispersed by the said solubilizer is not aggregated. Resultantly, physical stability of paclitaxel is obtained and not reduced in the lapse time.

In accordance with the present invention, polyoxyl hydrogenated castor oil is used as solubilizer. The said polyoxyl hydrogenated castor oil is a non-ionic surfactant prepared by converting castor oil to hard oil by hydrogenation, and condensing the said hard oil and ethylene oxide.

In the common compositions, carbonyl group of the paclitaxel is attacked by carboxylate anion in Cremophor EL and the paclitaxel is decomposed to Baccatin and ethyl ester compound. However, the said polyoxyl hydrogenated castor oil lowers reactivity of carboxylate anion and increases the stability of the paclitaxel. Also, without preliminary process that the said anion is contacted with aluminum oxide, the content of the carboxylate anion is below or equal to $0.6 \times 10^{-6}$ equivalent/ml by using polyoxyl hydrogenated castor oil.

The said polyoxyl hydrogenated castor oil is classified according to the average mole of added ethylene oxide. The average mole of added ethylene oxide is preferably 40, 50 and 60. More preferably, polyoxyl ethylene glycerol trihydroxystearate, polyoxyl hydrogenated castor oil prepared by using 60 mole of ethylene oxide on the average is used. The said polyoxyl hydrogenated castor oil is in a condition that pH is 4.5 to 8.0, and functions to improve the stability of paclitaxel.

Considering the function, dispersibility and viscosity of the effective vehicle, the mixed solution of the said polyoxyl hydrogenated castor oil and anhydrous ethanol is prepared by adding 95~99.89 weight percent of the total weight of the injectable compositions to paclitaxel. Preferably, the said polyoxyl hydrogenated castor oil and anhydrous oil are mixed in a ratio of 30:70~70:30 in volume/volume. More preferably, the ratio in volume/volume is 50:50.

Also, to prevent titer from lowering by decomposition of unstable paclitaxel, the stabilizer according to the present invention is added in the process for preparing the injectable compositions of paclitaxel. Any common stabilizers added to injectable compositions of paclitaxel are used as the said stabilizer. Particularly, organic acid, inorganic acid, polysorbate, ethanolamine, arginine, lysine and N-acetyl amino acids are used as the said stabilizers. Organic acid is selected from the group consisting of acetic acid, tartaric acid, ascorbic acid, sulfonic acid and citric acid. Inorganic acid is selected from the group consisting of Hydrochloric acid, Hydrobromic acid, Hydrofluoric acid, sulfuric acid and nitric acid.

pH of the said stabilizer is in a range of 8 and below, preferable 6.0~7.5, to prevent titer from lowering caused by decomposition of paclitaxel.

Also, for the stability of paclitaxel and pH control, 0.01~1.0 weight percent of the said stabilizer relative to the total weight of the composition is added to the injectable composition of paclitaxel.

Also, the present invention provides injectable compositions of paclitaxel comprising 0.1~5.0 weight percent of paclitaxel, 95~99.89 weight percent of a solution prepared by mixing solubilizer and anhydrous ethanol, and 0.01~1.0 weight percent of N-acetyl amino acid.

Any common solubilizers usually comprising injectable compositions of paclitaxel are used as the said solubilizer. Preferably, polyoxyl castor oil, polyoxyl hydrogenated castor oil, and poloxamer is used as the said solubilizer. The said polyoxyl castor oil is Cremophor EL or polyethoxylated castor oil (hereinafter referred to as Cremophor ELP™). The said polyoxyl hydrogenated castor oil is prepared by hydrogenating polyoxyl castor oil with ethylene oxide, wherein 40, 50 or 60 mol of ethylene oxide is used. Also, the poloxamer is a copolymer of polyethylene-propylene glycol.

The solution prepared by mixing the said solubilizer and anhydrous ethanol in a regular ratio is used in the process. Considering the function, dispersibility and viscosity of effective vehicle, 95~99.89 weight percent of the said solution is added to the compositions relative to the total weight of the injectable composition. Preferably, the said solubilizer and anhydrous oil are mixed in a ratio of 30:70~70:30 in volume/volume. More preferably, the ratio in volume/volume is 50:50.

N-acetyl amino acids as the stabilizer according to the present invention are added to the injectable compositions of paclitaxel to improve the stability of paclitaxel. pH of N-acetyl amino acid is in a range of 8 and below, preferable 6.0~7.5, thus to prevent titer caused by decomposition of paclitaxel from lowering.

The common stabilizer has danger in the safety in case of excessive use. However, the said N-acetyl amino acid is contained in nutrition solution, thus stability or safety of paclitaxel is excellent. According to the result of the toxicity test in rat, $LD_{50}$ of N-acetyl cysteine or citric acid was 3600 mg/kg or 42 mg/kg, respectively. These results show that N-acetyl cysteine has lower toxicity than citric acid by 90 times. Thus the injectable compositions of paclitaxel prepared by using N-acetyl amino acid as stabilizer have more stability than the common ones.

Particularly, the said N-acetyl amino acid is selected from the groups consisting of N-acetyl valine, N-acetyl proline, N-acetyl alanine, N-acetyl tryptophan and N-acetyl cysteine. More preferably, N-acetyl cysteine is used as the stabilizer.

Also, for stability and pH control of paclitaxel, 0.01~1.0 weight percent of the said N-acetyl amino acid is added to the compositions relative to the total weight of the compositions.

The injectable compositions of paclitaxel comprising paclitaxel, polyoxyl hydrogenated castor oil as solubilizer, and N-acetyl amino acid as stabilizer according to the present invention have more than efficacy compared with one of the common compositions. Also, the said compositions have low toxicity as well as the improved solubility and stability at the room temperature. For fineness of particle size, the said compositions can be administered to the body by intravenous injection.

AS shown in experimental examples, in case of the compositions prepared by adding Cremophor EL, residual percentage of paclitaxel decreased by 24% at 50° C. in 4 weeks. However, in case of the compositions prepared by adding polyoxyl hydrogenated castor oil as solubilizer according to the present invention, residual percentage of paclitaxel decreased by 5% at 50° C. in 4 weeks. The results show that the compositions of the present invention have the stability by 5 times. Also, in case of the compositions prepared by adding N-acetyl amino acid as stabilizer, residual percentage of paclitaxel decreased by 2~3% at 50° C. in 4 weeks. In case of the compositions prepared by adding N-acetyl amino acid as stabilizer, residual percentage of paclitaxel decreased by 2~3% at 50° C. in 4 weeks. Also, in case of the diluted solution prepared by diluting the composition with physiological saline by ten times, residual percentage of paclitaxel decreased by 2%. The result shows that paclitaxel has stability in the diluted solution.

Also, decrease of stability of paclitaxel results in the aggregation and precipitation among the paclitaxel, and increase of particle size. However, as shown in the experimental examples, particle size has no change in the solution and paclitaxel is stably dissolved in the compositions.

The said compositions are prepared by adding paclitaxel to the solution mixed the solubilizer and anhydrous ethanol in a ratio of 30:70~70:30, and therein adding the stabilizer.

175 mg/m$^2$ (300~500 mg in 60 Kg of adult) of the said compositions are diluted in physiological saline or glucose solution, and administered to the vein one time per 3 weeks. 1~5 ml of the said compositions containing 6~30 mg of paclitaxel are contained in the vial. Dosage of the composition according to the present invention depends on the contents of paclitaxel, administrative methods and therapeutic conditions. In case of adult, the content within 2~5 of vials is diluted in the physiological saline or glucose solution, and administered to the vein.

Hereunder is given the more detailed description of the present invention using examples. However, it should not be construed as limiting the scope of the present invention.

EXAMPLES 1~6

The Injectable Compositions of Paclitaxel Comprising Paclitaxel, Solubilizer and Anhydrous Ethanol

EXAMPLE 1

6 mg (0.6 weight percent) of paclitaxel was added to the solution of 527 mg (56.7 weight percent) of Cremophor EL and 0.5 ml of anhydrous ethanol. The mixture was stirred for 30 min to obtain the injectable composition of Paclitaxel.

EXAMPLE 2

Injectable Composition of Paclitaxel 2

6 mg (0.6 weight percent) of Paclitaxel was added to the solution of 527 mg (56.7 weight percent) of Cremophor ELP and 0.5 ml of anhydrous ethanol. The mixture was stirred for 30 min to obtain the injectable composition of Paclitaxel.

EXAMPLE 3

Injectable Composition of Paclitaxel 3

6 mg (0.6 weight percent) of Paclitaxel was added to the solution of 0.5 ml of anhydrous ethanol and 527 mg (56.7 weight percent) of polyoxyl hydrogenated castor oil (HCO 40®, hereinafter referred to as HCO 40) prepared by adding 40 mol of ethylene oxide to hard oil on the average. The mixture was stirred for 30 min to obtain the injectable composition of Paclitaxel.

EXAMPLE 4

Injectable Composition of Paclitaxel 4

6 mg (0.6 weight percent) of Paclitaxel was added to the solution of 0.5 ml of anhydrous ethanol and 527 mg (56.7 weight percent) of polyoxyl hydrogenated castor oil (HCO 60®, hereinafter referred to as HCO 60) prepared by adding 60 mol of ethylene oxide to hard oil on the average. The mixture was stirred for 30 min to obtain the injectable composition of Paclitaxel.

EXAMPLE 5

Injectable Composition of Paclitaxel 5

6 mg (0.6 weight percent) of Paclitaxel was added to the solution of 0.5 ml of anhydrous ethanol and 527 mg (56.7 weight percent) of polyethylene-propylene glycol copolymer, Pluronic L64® (BASF corporation). The mixture was stirred for 30 min to obtain the injectable composition of Paclitaxel.

EXAMPLE 6

Injectable Composition of Paclitaxel 6

6 mg (0.6 weight percent) of Paclitaxel was added to the solution of 0.5 ml of anhydrous ethanol and 527 mg (56.7 weight percent) of polyethylene-propylene glycol copolymer, Pluronic L44® (BASF corporation). The mixture was stirred for 30 min to obtain the injectable composition of Paclitaxel.

EXAMPLES 7~10

Injectable Composition of Paclitaxel Comprising Paclitaxel, Solubilizer, N-acetyl Proline and Anhydrous Ethanol

EXAMPLE 7

Injectable Composition of Paclitaxel 7

6 mg (0.6 weight percent) of Paclitaxel was added to the solution of 527 mg (56.7 weight percent) of Cremophor EL and 0.5 ml of anhydrous ethanol. The mixture was stirred for 30 min to dissolve paclitaxel absolutely. 0.5 mg (0.05 weight percent) of N-acetyl proline was added therein to obtain the injectable composition of Paclitaxel.

EXAMPLE 8

Injectable Composition of Paclitaxel 8

6 mg (0.6 weight percent) of Paclitaxel was added to the solution of 527 mg (56.7 weight percent) of Cremophor ELP and 0.5 ml of anhydrous ethanol. The mixture was stirred for 30 min to dissolve paclitaxel absolutely. 0.5 mg (0.05 weight percent) of N-acetyl proline was added therein to obtain the injectable composition of Paclitaxel.

EXAMPLE 9

Injectable Composition of Paclitaxel 9

6 mg (0.6 weight percent) of Paclitaxel was added to the solution of 527 mg (56.7 weight percent) of HCO 60 and 0.5 ml of anhydrous ethanol. The mixture was stirred for 30 min to dissolve paclitaxel absolutely. 0.5 mg (0.05 weight percent) of N-acetyl proline was added therein to obtain the injectable composition of Paclitaxel.

EXAMPLE 10

Injectable Composition of Paclitaxel 10

6 mg (0.6 weight percent) of Paclitaxel was added to the solution of 527 mg (56.7 weight percent) of HCO 40 and 0.5 ml of anhydrous ethanol. The mixture was stirred for 30 min to dissolve paclitaxel absolutely. 0.5 mg (0.05 weight percent) of N-acetyl proline was added therein to obtain injectable composition of Paclitaxel.

EXAMPLES 11~14

Injectable Composition of Paclitaxel Comprising Paclitaxel, HCO 60, N-acetyl Amino Acid and Anhydrous Ethanol

EXAMPLE 11

Injectable Composition of Paclitaxel 11

6 mg (0.6 weight percent) of Paclitaxel was added to the solution of 527 mg (56.7 weight percent) of HCO 60 and 0.5 ml of anhydrous ethanol. The mixture was stirred for 30 min to dissolve paclitaxel absolutely. 1.2 mg (0.1 weight percent) of N-acetyl valine was added therein to obtain the injectable composition of Paclitaxel.

EXAMPLE 12

Injectable Composition of Paclitaxel 12

6 mg (0.6 weight percent) of Paclitaxel was added to the solution of 527 mg (56.7 weight percent) of HCO 60 and 0.5 ml of anhydrous ethanol. The mixture was stirred for 30 min to dissolve paclitaxel absolutely. 0.75 mg (0.1 weight percent) of N-acetyl alanine was added therein to obtain the injectable composition of Paclitaxel.

EXAMPLE 13

Injectable Composition of Paclitaxel 13

6 mg (0.6 weight percent) of Paclitaxel was added to the solution of 527 mg (56.7 weight percent) of HCO 60 and 0.5 ml of anhydrous ethanol. The mixture was stirred for 30 min to dissolve paclitaxel absolutely. 0.1 mg (0.1 weight percent) of N-acetyl tryptophan was added therein to obtain the injectable composition of Paclitaxel.

EXAMPLE 14

Injectable Composition of Paclitaxel 14

6 mg (0.6 weight percent) of Paclitaxel was added to the solution of 527 mg (56.7 weight percent) of HCO 60 and 0.5 ml of anhydrous ethanol. The mixture was stirred for 30 min to dissolve paclitaxel absolutely. 0.6 mg (0.1 weight percent) of N-acetyl cysteine was added therein to obtain the injectable composition of Paclitaxel.

COMPARATIVE EXAMPLE

Conservative Injectable Composition of Taxol (Derived from Faulding Corporation)

6 mg (0.6 weight percent) of Paclitaxel was added to the solution of 527 mg (56.7 weight percent) of Cremophor EL 527 and 0.5 ml of anhydrous ethanol. The mixture was stirred for 30 min to dissolve paclitaxel absolutely. 0.2 mg (0.2 weight percent) of citric acid was added therein to obtain the injectable composition of Paclitaxel. ph of the said composition is 6.0.

Test of stability of the injectable composition derived from Faulding corporation showed that residual percentage of paclitaxel decreased by 6.56 percent, the particle size of the said composition is 10.0 nm.

EXPERIMENTAL EXAMPLE 1

Measurement of Residual Percentage of Paclitaxel According to Solubilizer

To measure stability of paclitaxel according to solubilizer, residual percentages of paclitaxel in injectable compositions of paclitaxel prepared by the said experiment 1~6 were measured.

The injectable compositions of paclitaxel composing paclitaxel and solubilizer were disposed for one, two and four weeks at 50, respectively. Residual percentages of the disposed compositions were measured by high performance liquid chromatography. The results were shown in Table 1.

TABLE 1

| | | Residual percentage of paclitaxel (%) | | | |
|---|---|---|---|---|---|
| Example | solubilizer | initiation | After 1 week | After 2 weeks | After 4 weeks |
| 1 | Cremophor EL | 100.59 | 91.24 | 86.70 | 74.42 |
| 2 | Cremophor ELP | 103.72 | 97.20 | 90.77 | 85.94 |
| 3 | HCO 40 | 98.99 | 93.55 | 88.23 | 78.98 |
| 4 | HCO 60 | 99.69 | 98.50 | 97.09 | 94.93 |
| 5 | Pluronic L64 | 99.76 | 98.58 | 97.28 | 96.41 |
| 6 | Pluronic L44 | 99.76 | 99.81 | 97.97 | 96.79 |

As shown in Table 1, in case of Cremophor EL as solubilizer, residual percentage of paclitaxel decreased by 26.27% compared with the initiation. The result of Cremophor EL showed maximum decrease of residual percentage of paclitaxel. In injectable composition of paclitaxel prepared by using solubilizer such as HCO 60, Pluronic L64 and Pluronic L64, residual percentage of paclitaxel decreased by 5% or lower. Thus the said solubilizer increased the stability of paclitaxel.

EXPERIMENTAL EXAMPLE 2

Measurement of Residual Percentage of Paclitaxel According to Stabilizer

To measure stability of paclitaxel according to addition of stabilizer, residual percentages of paclitaxel in injectable compositions of paclitaxel prepared by experiments 7–10 were measured.

The injectable compositions of paclitaxel composing paclitaxel, solubilizer and stabilizer as N-acetyl proline were disposed for one, two and four weeks at 50, respectively. Residual percentages of the disposed compositions were measured by high performance liquid chromatography. The results were shown in Table 2.

TABLE 2

Residual percentage of paclitaxel (%)

| Experiment | solubilizer | Stabilizer | initiation | After 1 week | After 2 weeks | After 4 weeks |
|---|---|---|---|---|---|---|
| 7 | Cremophor EL | N-acetyl proline | 99.33 | 94.91 | 91.57 | 84.33 |
| 8 | Cremophor ELP | N-acetyl proline | 101.45 | 100.67 | 96.82 | 96.28 |
| 9 | HCO 60 | N-acetyl proline | 101.87 | 100.52 | 99.76 | 98.05 |
| 10 | HCO 40 | N-acetyl proline | 98.07 | 97.34 | 95.25 | 93.44 |
| Comparative | Cremophor EL | Citric acid | 102.17 | 97.61 | 96.34 | 95.61 |

As shown in Table 2, in case of addition of N-acetyl proline as stabilizer, residual percentage of paclitaxel increased by twice compared with the ones of experiment 1–4. The result showed that stability of paclitaxel improved in case of adding solubilizer and stabilizer such as N-acetyl proline.

Also, comparative experiment showed residual percentage of injectable composition of taxol commercially available. In the comparative experiment, residual percentage of paclitaxel decreased by 6.56% in 4 weeks. However, in experiment 8, residual percentage of paclitaxel decreased by 3.82% in the same period. Resultantly, in case of adding N-acetyl proline as stabilizer, residual percentage of paclitaxel increased by twice.

EXPERIMENTAL EXAMPLE 3

Measurement of Residual Percentage of Paclitaxel According to N-acetyl Amino Acid Residual percentages of paclitaxel were measured in the injectable compositions of paclitaxel prepared by adding respective N-acetyl amino acid, as described in experiments 9 and 11–14.

The injectable compositions of paclitaxel composing paclitaxel, solubilizer and stabilizer as N-acetyl amino acid were disposed for one, two and four weeks at 50, respectively. Residual percentages of the disposed compositions were measured by high performance liquid chromatography. The results were shown in Table 3.

TABLE 3

Residual percentage of paclitaxel (%)

| Exp. | Solubilizer | Stabilizer | Initiation | After 1 week | After 2 weeks | After 4 weeks |
|---|---|---|---|---|---|---|
| 9 | HCO 60 | N-acetyl proline | 101.87 | 100.52 | 99.76 | 98.05 |
| 11 | HCO 60 | N-acetyl valine | 101.14 | 101.01 | 100.49 | 98.94 |
| 12 | HCO 60 | N-acetyl alanine | 101.63 | 100.02 | 99.80 | 98.13 |
| 13 | HCO 60 | N-acetyl tryptophan | 101.72 | 99.57 | 98.66 | 98.33 |
| 14 | HCO 60 | N-acetyl cycteine | 101.12 | 100.79 | 100.17 | 99.21 |

As shown in Table 3, in case of adding stabilizer such as N-acetyl amino acid, residual percentage of paclitaxel decreased by 5% or lower in 4 weeks. Particularly, in case of adding N-acetyl valine or N-acetyl cycteine as stabilizer, residual percentage of paclitaxel decreased by 2.2% or 1.91% respectively. The result showed that N-acetyl valine or N-acetyl cycteine improved the stability of paclitaxel relative to the other N-acetyl amino acids.

EXPERIMENTAL EXAMPLE 4

Dilution Test

Injectable composition of paclitaxel is administered to the body, by diluting the compositions in physiological saline or 5% of glucose solution to 10 times. To observe the stability of the paclitaxel in the diluted solution, injectable compositions of paclitaxel prepared in the said experiments were diluted in physiological saline solution in a ratio of one to ten. Residual percentages of the disposed compositions were measured by high performance liquid chromatography. The results were shown in Table 4.

TABLE 4

Residual percentage of paclitaxel in diluted solution (%)

| Exp. | solubilizer | stabilizer | After 0 hours | After 10 hours | After 30 hours |
|---|---|---|---|---|---|
| 1 | Cremophor EL | — | 97.93 | 96.72 | 95.09 |
| 2 | Cremophor ELP | — | 100.07 | 100.00 | 97.75 |
| 8 | Cremophor ELP | N-acetyl proline | 99.07 | 97.34 | 96.04 |
| 9 | HCO 60 | N-acetyl proline | 99.48 | 99.05 | 97.16 |
| 10 | HCO 40 | N-acetyl proline | 100.25 | 100.08 | 98.50 |

As shown in Table 4, in case of the said diluted solution, residual percentage of paclitaxel decreased by 3% or lower. Particularly, in case of the diluted solution prepared by using HCO 40 as stabilizer, residual percentage of paclitaxel decreased by 1.75%. The result showed that HCO 40 as stabilizer provided maximum stability of paclitaxel in the compositions.

EXPERIMENTAL EXAMPLE 5

Measurement of Particle Size

To observe change of particle size of paclitaxel in according to the lapse time, injectable compositions of paclitaxel prepared in experiments 1–16 were diluted by adding distilled water to the compositions. The particle size of paclitaxel in the diluted solution was measured. The results were shown in Table 5.

TABLE 5

| Exp. | Initiation(nm) | After 4 weeks(nm) |
|---|---|---|
| 1 | 13.2 | 10.4 |
| 2 | 17.7 | 17.7 |
| 3 | 11.2 | 10.0 |
| 4 | 10.2 | 10.8 |
| 5 | 227.40 | 242.2 |
| 6 | 167.20 | 211.1 |
| 7 | 9.8 | 11.0 |
| 8 | 10.0 | 10.6 |
| 9 | 21.5 | 19.7 |
| 10 | 13.8 | 12.9 |
| 11 | 21.0 | 16.6 |
| 12 | 19.9 | 20.8 |

TABLE 5-continued

| Exp. | Initiation(nm) | After 4 weeks(nm) |
|---|---|---|
| 13 | 25.2 | 16.4 |
| 14 | 22.7 | 22.6 |
| 15 | 18.0 | 16.9 |
| 16 | 18.4 | 16.9 |

As shown in Table 5, particle size compared with the initiation in 4 weeks. If stability of paclitaxel decreases in the diluted solution, particle size of paclitaxel increased by the aggregation or precipitation of paclitaxel. Thus the result showed that paclitaxel is dissolved in the diluted solution without aggregation or precipitation.

EXPERIMENTAL EXAMPLE 6

Toxicity Test of Injectable Compositions of Paclitaxel in Rats 4-week old ICR line male rats were used in the toxicity test of injectable compositions of paclitaxel.

In case of injectable compositions of paclitaxel composing paclitaxel, HCO 60 and N-acetyl cysteine, dosages registered in Table 6 were administered to the tail of rats by intravenous injection. Also, Taxol® derived from (Bristol-Myers Squibb corporation) was administered to the tail of rats be the same procedure. The toxicity test above proceeded for 2 weeks. The results are shown in Table 6.

TABLE 6

| composition | Dosage (mg) | Total rats | Deceased rat (days) | Survived rat | Survival ratio (%) | $LD_{50}$ |
|---|---|---|---|---|---|---|
| Exp. 9 | 45 | 4 | 1 (0) | 3 (14) | 75 | >45 |
| Exp. 9 | 30 | 4 | 0 | 4 (14) | 100 | >45 |
| Exp. 9 | 20 | 4 | 0 | 4 (14) | 100 | >45 |
| Exp. 9 | 13 | 4 | 0 | 4 (14) | 100 | >45 |
| Exp. 9 | 9 | 4 | 0 | 4 (14) | 100 | >45 |
| Exp. 9 | 6 | 4 | 0 | 4 (14) | 100 | >45 |
| Exp. 9 | 4 | 4 | 0 | 4 (14) | 100 | >45 |
| Exp. 9 | Vehicle | 4 | 2 (3), 1 (10) | 4 (14) | 25 | >45 |
| Taxol ® | 45 | 4 | 2 (0) | 2 (14) | 50 | 45 |
| Taxol ® | 30 | 4 | 2 (0) | 2 (14) | 50 | 45 |
| Taxol ® | 20 | 4 | 1 (5) | 3 (14) | 75 | 45 |
| Taxol ® | 13 | 4 | 0 | 4 (14) | 100 | 45 |
| Taxol ® | 9 | 4 | 0 | 4 (14) | 100 | 45 |
| Taxol ® | 6 | 4 | 0 | 4 (14) | 100 | 45 |
| Taxol ® | 4 | 4 | 0 | 4 (14) | 100 | 45 |
| Taxol ® | Vehicle | 4 | 1 (0), 1 (5), 1 (8) | 1 (14) | 25 | 45 |

Injectable compositions of paclitaxel prepared by using solubilizer such as HCO 60, and stabilizer such as N-acetyl cysteine as in experiment 9 were administered to the rats by intravenous injection. As shown in Table 6, 30 mg and 45 mg of injectable composition resulted in 100% and 75% of the survival ratio respectively. Also, in case of the above, $LD_{50}$ was registered to 45 mg or higher. 20 mg, 30 mg and 45 mg of Taxol® resulted in 75%, 50% and 50% respectively. In case of the above, $LD_{50}$ was registered to 45 mg.

The results showed that due to low toxicity of HCO 60 and stability of N-acetyl cysteine, injectable composition composing HCO 60 and N-acetyl cysteine, according to the present invention has lower toxicity than common injectable composition prepared by mixing paclitaxel with Cremophor EL as solubilizer.

INDUSTRIAL APPLICABILITY

As described above, the present invention provided the processes by preparing injectable compositions of paclitaxel comprising paclitaxel, anhydrous ethanol, solubilizer such as polyoxyl hydrogenated castor oil, and stabilizer such as N-acetyl amino acid. The said compositions have more than efficacy compared with one of the common compositions. Also, the said compositions have low toxicity as well as the improved stability at the room temperature. Thus the injectable compositions of paclitaxel according to the present invention were used as antitumor agents usefully.

What is claimed is:

1. An injectable composition comprising paclitaxel, polyoxyl hydrogenated castor oil, N-acetyl amino acid, and anhydrous ethanol.

2. The injectable compositions according to claim 1, wherein the polyoxyl hydrogenated castor oil is prepared by adding ethylene oxide whose average number of mole is 40, 50, or 60.

3. The injectable composition according to claim 2, wherein the polyoxyl hydrogenated castor oil is prepared by adding ethylene oxide whose average number of mole is 60.

4. The injectable compositions according to claim 1, wherein pH of the said compositions is in a range form 6.0 to 8.0.

5. The injectable composition according to claim 1, wherein the N-acetyl amino acid is N-acetyl valine, N-acetyl proline, N-acetyl alanine, N-acetyl tryptophan, or N-acetyl cysteine.

6. The injectable composition according to claim 5, wherein the N-acetyl amino acid is N-acetyl cysteine.

* * * * *

UNITED STATES PATENT AND TRADEMARK OFFICE
CERTIFICATE OF CORRECTION

PATENT NO. : 7,186,751 B2 Page 1 of 1
APPLICATION NO. : 10/489224
DATED : March 6, 2007
INVENTOR(S) : Lee et al.

It is certified that error appears in the above-identified patent and that said Letters Patent is hereby corrected as shown below:

Column 12
Line 42, "form" should read as --from--.

Signed and Sealed this

Fifteenth Day of April, 2008

JON W. DUDAS
*Director of the United States Patent and Trademark Office*